United States Patent [19]

Manara

[11] Patent Number: 5,236,951
[45] Date of Patent: Aug. 17, 1993

[54] PHARMACEUTICAL COMPOSITIONS FOR THE TREATMENT OF OCULAR DISORDERS

[75] Inventor: Luciano Manara, Pietra Marazzi-Alessandria, Italy

[73] Assignee: Sanofi, Paris, France

[21] Appl. No.: 536,741

[22] Filed: Jun. 12, 1990

[30] Foreign Application Priority Data

Jun. 13, 1989 [FR] France ................ 8907816
Jun. 13, 1989 [FR] France ................ 8907817

[51] Int. Cl.$^5$ ............ A61K 31/21; A61K 31/195; A61K 31/165; A61K 31/135

[52] U.S. Cl. ............................ 514/510; 514/567; 514/617; 514/649; 514/654; 514/657; 514/913

[58] Field of Search ............ 514/657, 510, 567, 617, 514/649, 654, 657, 413

[56] References Cited

U.S. PATENT DOCUMENTS 3,808,317 4/1974 Hecht .................... 514/913

Primary Examiner—Zohreh A. Fay
Attorney, Agent, or Firm—Bacon & Thomas

[57] ABSTRACT

A method of prophylaxis and/or of treatment of ocular disorders, mainly of controlling intraocular hypertension and treating glaucoma, which comprises administering, preferably topically, a prophylactically and/or therapeutically effective amount of a phenylethanolamine derivative.

12 Claims, No Drawings

PHARMACEUTICAL COMPOSITIONS FOR THE TREATMENT OF OCULAR DISORDERS

The present invention relates to a method for the prophylaxis and/or treatment of ocular disorders by using certain phenylethanolamine derivatives or their pharmaceutically acceptable salts. More particularly the present invention refers to a method for the prophylaxis and/or treatment of ocular hypertension and glaucoma. The present invention also concerns the pharmaceutical compositions suitable for these indications. Glaucoma is an ocular disorder characterized, among other symptoms, also by an increase, either slow or fast, in intraocular pressure. Glaucoma leads to a damage of the optical nerve fibers and may ressort in loss of the visual function. One of the most common methods of treating glaucoma concentrates on reducing intraocular pressure. However, the drugs which are actually used for the treatment of glaucoma proved of difficult use. As an example, pilocarpine has local side-effects while other active principles such as epinephrine or the beta-adrenergic blocking agent, timolol, are not acceptable to certain patients who are affected by cardiovascular diseases or who do not stand the systemic cardiovascular effects of said drugs.

| | | | |
|---|---|---|---|
| EP-A-6,735, | EP-A-7,204, | EP-A-21,636, | EP-A-23,385, |
| EP-A-25,331, | EP-A-28,105, | EP-A-40,000, | EP-A-40,915, |
| EP-A-52,936, | EP-A-61,907, | EP-A-63,004, | EP-A-66,351, |
| EP-A-68,669, | EP-A-70,133, | EP-A-70,134, | EP-A-89,154, |
| EP-A-91,749, | EP-A-95,827, | EP-A-99,707, | EP-A-101,069, |
| EP-A-140,359, | EP-A-146,392, | EP-A-164,700, | EP-A-170,121, |
| EP-A-170,135, | EP-A-171,519, | BE-A-900,983, | UK-A-2,133,986, |
| AU-A-8431944, | WO-A-8400956, | and US-A-4,391,826 | | describe some phenylethanolamine derivatives, optionally to form ethers, esters or cyclic derivatives, with antihyperglycemic and/or antiobesity activity. EP-A-255,415 teaches that the phenylethanolamine derivatives described in these last patents, as well as their salts, may be employed for the preparation of pharmaceutical compositions active on the intestinal smooth muscle, suitable for the treatment of disorders associated with a smooth muscle contraction without producing any relevant cardiac or respiratory side-effect, provided said phenylethanolamine derivatives do not contain hydroxy groups on the phenyl ring of the phenylethanolamine moiety. EP-A-211,721, EP-A-303,545, and EP-A-303,546, describe phenylethanolamine derivatives characterized by the presence of a tetraline ring linked to the amino group, active as antiobesity and intestinal motility modulating agents. It has now been found that the phenylethanolamine derivatives described in the above quoted patents may be employed for the treatment of ocular disorders such as ocular hypertension and glaucoma.

Accordingly, the present invention concerns, in one of its embodiments, a method for the prophylaxis and/or treatment of ocular disorders, mainly for controlling intraocular pressure and for treating ocular hypertension and glaucoma, which comprises administering to a mammal in need thereof a prophylactically or therapeutically effective amount of a phenylethanolamine derivative having the following formula (I)

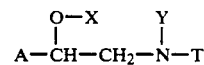

wherein

A represents a benzofuran-2-yl group or a phenyl group, both groups being either unsubstituted or substituted with one or two halogen atoms or with a lower alkyl or trifluoromethyl group;

X represents hydrogen, lower alkyl or lower alkanoyl;

Y represents hydrogen or a group A'—CH(OH)—CH$_2$—, A' being identical to A, but different from benzofuran-2-yl; or X and Y taken together form a methylene bridge optionally substituted with a carbo(lower alkoxy) group; an ethylene bridge optionally oxo-substituted; or a 1,3-propylene bridge; and T represents a group of formula (II)

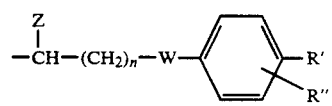

wherein
n is 1, 2, or 3;
Z is hydrogen or a lower alkyl group;
W represents a direct bond or an oxygen atom;
R' represents
. hydrogen
. lower alkyl
. a functional group selected from the group consisting of hydroxy; lower alkoxy; lower alkenyloxy; lower alkynyloxy; cycloalkyloxy; cycloalkyl-(lower alkoxy); benzyloxy; phenoxy; mercapto; (lower alkyl)thio; (lower alkenyl)thio; (lower alkynyl)thio; cycloalkylthio; cycloalkyl-(lower alkyl)thio; benzylthio; phenylthio; (lower alkyl)sulfinyl; (lower alkenyl)sulfinyl; (lower alkynyl)sulfinyl; cycloalkylsulfinyl; cycloalkyl-(lower alkyl)sulfinyl; benzylsulfinyl; phenylsulfinyl; (lower alkyl)sulfonyl; (lower alkenyl)sulfonyl; (lower alkynyl)sulfonyl; cycloalkylsulfonyl; cycloalkyl-(lower alkyl)sulfonyl; benzylsulfonyl; phenylsulfonyl; cyano; nitro; amino either unsubstituted or substituted with one or two radicals which are independently selected from the group consisting of lower alkyl, lower alkenyl, lower alkynyl, cycloalkyl, cycloalkyl-(lower alkyl), benzyl, and phenyl; carboxy; (lower alkoxy)carbonyl; (lower alkenyloxy)carbonyl; (lower alkynyloxy)carbonyl; cycloalkyloxycarbonyl; cycloalkyl-(lower alkoxy)-carbonyl; benzyloxycarbonyl; phenoxycarbonyl; and carbamoyl either unsubstituted or substituted on the amino group with one or two radicals independently selected from the group consisting of lower alkyl, lower alkenyl, lower alkynyl, cycloalkyl, cycloalkyl-(lower alkyl), benzyl, and phenyl;
- a radical -R selected from the group consisting of lower alkyl substituted with a functional group; lower alkenyl substituted with a functional group; lower alkynyl substituted with a functional group; phenyl-(lower alkyl) substituted on the phenyl ring with a lower alkyl or a functional group; phenyl-(lower alkenyl) substituted on the phenyl ring with a lower alkyl or a functional group; phenyl-(lower alkynyl) substituted on the phenyl ring with a lower alkyl or a functional group; benzyl substituted on the phenyl ring with a lower alkyl or a functional group; and phenyl either unsubstituted or substituted with a lower alkyl or a functional group; the functional group being as defined above; defined above;
- a group —OR, —SR, —SO—R, or —SO₂R wherein R is as defined above and.R° defined above;
- a group -NRR°, wherein R is as defined above and -R° represents hydrogen or is as defined above for -R, or R and R°, taken together with the nitrogen atom, may represent a group selected from pyrrolidino, piperidino and morpholino;
- a-COOR or -COSR group, wherein R is as defined above;
- a group-CONRR°, wherein R is as defined above and R° represents hydrogen or is as defined above for R, or R and R°, taken together with the nitrogen atom, may represent a group selected from pyrrolidino, piperidino and morpholino;
- a group-SO₂NRR°, wherein R is as defined above and R° represents hydrogen or is as defined above for R, or R and R°, taken together with the nitrogen atom, may represent a group selected from pyrrolidino, piperidino and morpholino; and R" represents
- hydrogen;
- a halogen atom;
- a lower alkyl group;
- a functional group as defined above;
- a group —OR, wherein R is as defined above;
- a group —COOR, wherein R is as defined above;
- a group —CONRR°, wherein R is as defined above and R° represents hydrogen or is as defined above for R, or R and R°, taken together with the nitrogen atom, may represent a group selected from pyrrolidino, piperidino and morpholino; or when A represents a phenyl group, either unsubstituted or substituted with a group selected from halogen, lower alkyl, and trifluoromethyl, and X and Y are hydrogen atoms, T may also represents a group of formula (III)

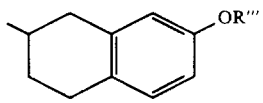

(III)

wherein
R'" represents hydrogen; methyl; or methyl substituted with carboxy or carbo(lower alkoxy). As used herein, the terms "lower alkyl", "lower alkenyl", and "lower alkynyl" designate monovalent radicals derived from aliphatic hydrocarbons of up to 4 carbon atoms, saturated or containing a double or triple bond, such as for instance methyl, ethyl, propyl, isopropyl, tert-butyl, allyl, crotyl, and propargyl. The term "cycloalkyl" identifies the monovalent radical of an alicyclic hydrocarbon of from 3 to 8 carbon atoms, cyclopropyl, cyclopentyl, and cyclohexyl radicals being preferred. The terms "lower alkoxy", "lower alkenyloxy", "lower alkynyloxy", "cycloalkyloxy" and the corresponding thio derivatives, as used herein, designate the hydroxy or a mercapto group etherified by a lower alkyl, lower alkenyl, lower alkynyl, or cycloalkyl group as defined above. The term "carbo(lower alkoxy)" designates a lower alkyl ester of a carboxy group, wherein the term lower alkyl is as defined above; more particularly the terms "carbalkoxy", "carbomethoxy" and "carbethoxy" are used herein as synonyms of the terms "alkoxycarbonyl", "methoxycarbonyl", and "ethoxycarbonyl" respectively. The term "lower alkanoyl" identifies a group carbonyl substituted with a lower alkyl group as defined above. The term "halogen" designates the four common halogens, i.e. fluorine, chlorine, bromine and iodine, fluorine and particularly chlorine being preferred. The compounds of formula (I) above may be in an optically inactive form or in optically active forms selected from the enantiomers, diastereoisomers, and their mixtures. All these compounds and their pharmaceutically acceptable salts may be employed in the method according to the present invention. The pharmaceutically acceptable salts of the compounds of formula (I), such as the hydrochloride, hydrobromide, sulfate, hydrogensulfate, dihydrogenphosphate, methanesulfonate, methylsulfate, oxalate, maleate, fumarate, naphthalen-2-sulfonate, and the like salts, may be obtained by treating the free base, dissolved for instance in an alcohol such as isopropanol, with a solution of the suitably selected acid in the same solvent. When the compound of formula (I) contains a free carboxy group, its amphoteric character allows the preparation of salts either with pharmaceutically acceptable acids or pharmaceutically acceptable bases. Salts with pharmaceutically acceptable bases are preferably the alkaline metal salts, such as the corresponding sodium salts, but salts with organic bases such as trometamol are also acceptable. For the purposes of the present invention a preferred group of compounds comprises those compounds of formula (I) wherein A represents unsubstituted phenyl or phenyl substituted with a group selected from the group consisting of halogen, lower alkyl, and trifluoromethyl;

X and Y are hydrogen; and

T represents a group of formula (III) wherein R'" is as defined above. An even more preferred group of compounds comprises those compounds of formula (I) wherein A is a 3-chlorophenyl group X and Y are hydrogen; and T represents a group of formula (III) wherein R'" is hydrogen; carbomethoxymethyl; or carbethoxymethyl. Particularly preferred active compounds are N-(7-hydroxy-1,2,3,4-tetrahydronaphth-2-yl)-2-(3-chlorophenyl)-2-hydroxyethanamine (Compound A) and its pharmaceutically acceptable salts (EP-A-211,721)

N-/[2S)-(7-hydroxy-1,2,3,4-tetrahydronaphth-2-yl]-(2R)-2-(3-chlorophenyl)-2-hydroxyethanamine (Compound B) and its pharmaceutically acceptable salts (EP-A-303,545)

N-[(2R)-(7-hydroxy-1,2,3,4-tetrahydronaphth-2-yl)]-(2R)-2-(3-chlorophenyl)-2-hydroxyethanamine (Compound C) and its pharmaceutically acceptable salts (EP-A-303,545)

N-[(2S)-(7-hydroxy-1,2,3,4-tetrahydronaphth-2-yl]-(2S)-2-(3-chlorophenyl)-2-hydroxyethanamine (Compound D) and its pharmaceutically acceptable salts (EP-A-303,545)

N-[(2R)-(7-hydroxy-1,2,3,4-tetrahydronaphth-2-yl](2S)-2-(3-chlorophenyl)-2-hydroxyethanamine (Compound E) and its pharmaceutically acceptable salts (EP-A-303,545)

N-[(2R)-7-ethoxycarbonylmethoxy-1,2,3,4-tetrahydronaphth-2-yl]-(2R)-2-(3-chlorophenyl)-2-hydroxyethanamine (Compound F) and its pharmaceutically acceptable salts (EP-A-303,546)

N-[(2S)-7-ethoxycarbonylmethoxy-1,2,3,4-tetrahydronaphth-2-yl]-(2R)-2-(3-chlorophenyl)-2-hydroxyethanamine (Compound G) and its pharmaceutically acceptable salts (EP-A-303,546)

N-[(2S)-7-ethoxycarbonylmethoxy-1,2,3,4-tetrahydronaphth-2-yl]-(2S)-2-(3-chlorophenyl)-2-hydroxyethanamine (Compound H) and its pharmaceutically acceptable salts (EP-A-303,546) and N-[(2R)-7-methoxycarbonylmethoxy-1,2,3,4-tetrahydronaphth-2-yl]-(2R)-2-(3-chlorophenyl)-2-hydroxyethanamine (Compound I) and its pharmaceutically acceptable salts (EP-A-303,546).

Another preferred group of compounds according to the invention comprises those compounds of formula (I) wherein A is phenyl, 2-fluorophenyl, 3-chlorophenyl, or 3-trifluoromethylphenyl;

X is hydrogen;

Y is hydrogen or a group A'—CH(OH)—CH$_2$— wherein A' is the same as A and is phenyl, 2-fluorophenyl, 3-chlorophenyl, or 3-trifluoromethylphenyl;

T is a group of formula (II) wherein n is 1 or 2;

R' is

. a functional group selected from hydroxy; carboxy; carbo(lower alkoxy); and carbamoyl; or . a group —OR wherein R is a lower alkyl or lower alkenyl group substituted with a functional group selected from carboxy and carbo(lower alkoxy);

R" is hydrogen;

W is a direct bond; and

Z is a lower alkyl group, preferably methyl.

An even more preferred group of compounds for the use according to the invention comprises those compounds of formula (I) wherein A is phenyl, 3-chlorophenyl, or 3-trifluoromethylphenyl;

X is hydrogen;

Y is hydrogen or a group A'—CH(OH)—CH$_2$— wherein A' is the same as A and is phenyl;

T is a group of formula (II) wherein n is 1 or 2;

R' is selected from the group consisting of hydroxy, carboxy, carbomethoxy, carbethoxy, carbamoyl, carboxymethoxy, carbomethoxymethoxy and carbethoxymethoxy;

R" is hydrogen;

W is a direct bond; and

Z is methyl.

Among these compounds particularly advantageous compounds are

N-[2-(4-carbomethoxyphenyl)-1-methylethyl/-2-hydroxy-2-phenylethylamine (Compound J), described in Example 21 of EP-B-6,735, as the lower melting diastereoisomer mixture prepared as described in "Description 15" of EP-B-21,636, and its pharmaceutically acceptable salts, particularly the neutral fumarate;

N-[2-(4-carboxyphenyl)-1-methylethy]-2-hydroxy-2-phe-nylethylamine (Compound K), prepared by saponification of Compound J, and its pharmaceutically acceptable salts;

(R,S)-N-(2-phenyl-2-hydroxyethyl)-1-methyl-3-(4-hydroxy phenyl)propylamine (Compound L), described in Example 10 of U.S. Pat. No. 4,391,826, and its pharmaceutically acceptable salts, particularly the hydrochloride;

(R,S)-N-(2-phenyl-2-hydroxyethyl)-1-methyl-3-(4-aminocarbonylphenyl)propylamine (Compound M), described in Example 15 of U.S. Pat. No. 4,391,826, and its pharmaceutically acceptable salts, particularly the hydrochloride;

p-[(R)-3-[bis-[(R)-beta-hydroxyphenethyl]amino]-butyl]benzamide (Compound N), described in Example 12 of EP-A-101,069, and its pharmaceutically acceptable salts, particularly the maleate and the fumarate;

p-[(S)-3-[bis-[(R)-beta-hydroxyphenethyl]amino]-butyl]benzamide (Compound O), described in Example 8 of EP-A-101,069, and its pharmaceutically acceptable salts;

(RR,SS)-N-[2-(4-carbomethoxyphenyl)-1-methylethyl]-2-hydroxy-2-(3-trifluoromethylphenyl)ethanamine (Compound P), described in Example 19 of EP-B-40,915, and its pharmaceutically acceptable salts;

(RR,SS)-N-[2-(4-carboxyphenyl)-1-methylethyl]-2-hydroxy-2-(3-trifluoromethylphenyl)ethanamine (Compound Q), prepared by saponification of Compound P, and its pharmaceutically acceptable salts;

N-[2-(4-carbomethoxymethoxyphenyl)-1-methylethyl]-2-hydroxy-2-(3-chlorophenyl)ethanamine (Compound R), described in Example 6 of EP-B-23,385, and its pharmaceutically acceptable salts, particularly the hydrobromide of its (RR,SS) form ("Description 21" of EP-B-70,133);

N-[2-(4-carboxymethoxyphenyl)-1-methylethyl]-2-hydroxy-2-(3-chlorophenyl)ethanamine (Compound S), prepared by saponification of Compound R, and its pharmaceutically acceptable salts. The compounds of formula (I) above can be prepared as described in the following patent references:

| EP-A-6,735, | EP-A-7,204, | EP-A-21,636, | EP-A-23,385, |
|---|---|---|---|
| EP-A-25,331, | EP-A-28,105, | EP-A-40,000, | EP-A-40,915, |
| EP-A-52,936, | EP-A-61,907, | EP-A-63,004, | EP-A-66,351, |
| EP-A-68,669, | EP-A-70,133, | EP-A-70,134, | EP-A-89,154, |
| EP-A-91,749, | EP-A-95,827, | EP-A-99,707, | EP-A-101,069, |
| EP-A-140,359, | EP-A-146,392, | EP-A-164,700, | EP-A-170,121, |
| EP-A-170,135, | EP-A-171,519, | EP-A-211,721, | EP-A-255,415, |
| EP-A-303,545, | EP-A-303,546, | BE-A-900,983, | UK-A-2,133,986, |
| AU-A-8431944, | WO-A-8400956, | and US-A-4,391,826. | |

The compounds of formula (I) as well as their pharmaceutically acceptable salts are poorly toxic. Their acute toxicity is well below the therapeutically active dose. They are well tolerated locally following ocular administration. In particular, some compounds of formula (I) are indicated as potential therapeutic agents in the treatment of obesity (Nature, 1984, 309,163–165) and one of them has been tested in clinic (Int. J. Obesity, 1985, 9,230; ibid. 1985, 9, 231). The present invention also concerns, in another embodiment thereof, a method for treating ocular disorders, particularly for controlling intraocular pressure and for treating ocular hypertension and glaucoma in mammals, including humans, said method comprising administering to said mammals an effective amount of a compound of formula (I) or of one of its pharmaceutically salts. The invention also concerns the use of a phenylethanolamine derivative of formula (I) or of one of its pharmaceutically acceptable salts thereof in combination with another active principle suited for the treatment of glaucoma. The active principle used in combination with the compound of the invention may be an antiinflammatory agent, particularly a steroid or corticosteroid antinflammatory agent used in the treatment of glaucoma, a side effect of which is an increase in intraocular pressure. The present invention also concerns therefore a pharmaceutical composition containing a phenylethanolamine derivative of formula (I) or one of its pharmaceutically acceptable salts for controlling the increase in intraocular pressure following a treatment with steroid antiinflammatory agents. The phenylethanolamine derivatives used according to the present invention are preferably formulated as ophthalmic pharmaceutical compositions to be administered topically to the eye, as solutions, suspensions or ointments. The ophthalmic compositions according to the invention may contain from 0.00001 to 1 % by wt., more particularly from 0.0001 to 0.2 % by wt., of a compound of the present invention. Each dosage unit (drop) contains from 10 ng to 1 mg, and preferably from 100 ng to 0.2 mg, of phenylethanolamine derivative. These preparations may be administered by applying, in the eye, 1 or 2 drops, 1 to 3 times a day, to provide a daily posology of from 10 ng to 1 mg, preferably of from 100 ng to 0.2 mg of active principle. The expression "controlling elevated intraocular pressure", as used herein, stands for normalizing, reducing and modulating high intraocular pressure (IOP) which is the earliest symptom in the diagnosis of glaucoma. The expression also means that the reduction in intraocular pressure obtained according to the invention by the use of a phenylethanolamine derivative of formula (I) or of one of its pharmaceutically acceptable salts lasts for a period of time sufficiently long, for instance inbetween two consecutive administrations. The IOP lowering effect of a pharmaceutical composition according to the invention may be evaluated in animals, as an example in the rabbit, by means of a test which involves oral administration of large amounts of water, such as that described in Arch. Ophthal., 1969,82,381–384, or in J. Ocul. Pharmacol., 1985, 1(2), 161–168; or rapid i.v. injection of a glucose solution, such as that described in Boll. Ocul., 1979, 58(7–8), 359–66. To obtain suitable preparations, the pharmaceutical compositions may be admixed with a carrier acceptable for a topical ophthalmic administration or for a systemic treatment. As pharmaceutical carriers acceptable for an ophthalmic topical administration, there may be cited water, mixtures of water and water-miscible solvents such as lower alkanols, vegetable oils, mineral oils which may contain from 0.5 to 5 % by wt. of hydroxyethylcellulose, ethyl oleate, carboxymethylcellulose, polyvinylpyrrolidone, and other water-soluble polymers, which are non toxic and compatible with an ophthalmic use, as an example cellulose derivatives, such as methylcellulose, carboxymethylcellulose alkali metal salts, hydroxymethylcellulose, hydroxyethylcellulose, hydroxypropylmethylcellulose, acrylates, such as polyacrylic acid salts, ethylpolyacrylates, polyacrylamides, natural products such as gelatin, alginates, pectines, tragacanth, karaya gum, chondrus, agar, acacia, starch derivatives such as starch acetate, hydroxyethyl starch ethers, hydroxypropyl starch, as well as other synthetic derivatives such as polyvinylalcohol, polyvinylpyrrolidone, polyvinylmethylether, polyethylene oxide, neutral carbopol, or xanthan, and their mixtures. The pharmaceutical preparation may also contain non-toxic auxiliary substances such as emulsifying, preserving, wetting, bodying agents and the like such as for instance polyethylene glycols 200, 300, 400, 600, carbowaxes 1000, 1500, 4000, 6000, 10000, antibacterial agents such as quaternary ammonium compounds, phenylmercuric salts known to have cold sterilizing properties and which are non-injurious in use, thimerosal, propylparaben, benzyl alcohol, phenyl ethanol, buffering agents, buffering agents such as alkali metal chlorides, borate, acetate, or gluconate buffers, antioxidants such as sodium metabisulfite, butylated hydroxyanisole, butylated hydroxytoluene, or the like agents and other agents typically used in this field such as sorbitan monolaurate, triethanolamine oleate, polyoxyethylene sorbitan monopalmytate, dioctyl alkali metal sulfosuccinate, monothioglycerol, ethylenediamine tetraacetic acid and the like. Additionally, suitable ophthalmic excipients may be employed such as for instance phosphate buffer, isotonic boric acid, isotonic alkaline chloride solutions or tromethamine. The pharmaceutical preparation may also be in the form of a suspension wherein the soluble particles are water-soluble or insoluble polymers. Such a suspension may contain microparticles or nanoparticles. The phenylethanolamine derivatives used according to the present invention may also be administered as pharmaceutical compositions for enteral or parenteral administration; said compositions and dosages are described in EP-A-211,721, and EP-A-255,415. The compositions according to the invention may contain additional active principles. Accordingly, antibiotics, anesthetics or other IOP lowering agents may be present. The following examples illustrate the invention without limiting it.

EXAMPLE 1

Ophthalmic solution:

| Compound G (as the hydrochloride) | 1.0 mg |
|---|---|
| NaH$_2$PO$_4$ | 10.4 mg |
| Na$_2$HPO$_4$ | 2.4 mg |
| chlorobutanol | 5.0 mg |
| hydroxypropylmethylcellulose | 5.0 mg |
| NaOH 1N q.s. to pH = 7.4 | |
| distilled water q.s. to | 1.0 ml |

The solution ingredients are mixed together according to the procedures conventionally employed for the preparation of ophthalmic solutions.

EXAMPLE 2

Ophthalmic solution:

| | |
|---|---|
| Compound F (as the hydrochloride) | 1.0 mg |
| NaH$_2$PO$_4$ | 10.4 mg |
| Na$_2$HPO$_4$ | 2.4 mg |
| chlorobutanol | 5.0 mg |
| hydroxypropylmethylcellulose | 5.0 mg |
| NaOH 1N q.s. to pH = 7.4 | |
| distilled water q.s. to | 1.0 ml |

The solution ingredients are mixed together according to the procedures conventionally employed for the preparation of ophthalmic solutions.

EXAMPLE 3

Ophthalmic solution:

| | |
|---|---|
| Compound G (as the hydrochloride) | 1.0 mg |
| Betamethasone sodium phosphate | 1.0 mg |
| NaH$_2$PO$_4$ | 10.4 mg |
| Na$_2$HPO$_4$ | 2.4 mg |
| chlorobutanol | 5.0 mg |
| hydroxypropylmethylcellulose | 5.0 mg |
| NaOH 1N q.s. to pH = 7.4 | |
| distilled water q.s. to | 1.0 ml |

The solution ingredients are mixed together according to the procedures conventionally employed for the preparation of ophthalmic solutions.

EXAMPLE 4

Ophthalmic solution:

| | |
|---|---|
| Compound J (as the neutral fumarate) | 1.0 mg |
| NaH$_2$PO$_4$ | 10.4 mg |
| Na$_2$HPO$_4$ | 2.4 mg |
| chlorobutanol | 5.0 mg |
| hydroxypropylmethylcellulose | 5.0 mg |
| NaOH 1N q.s. to pH = 7.4 | |
| distilled water q.s. to | 1.0 ml |

The solution ingredients are mixed together according to the procedures conventionally employed for the preparation of ophthalmic solutions.

EXAMPLE 5

Ophthalmic solution:

| | |
|---|---|
| Compound S (as the hydrobromide) | 1.0 mg |
| NaH$_2$PO$_4$ | 10.4 mg |
| Na$_2$HPO$_4$ | 2.4 mg |
| chlorobutanol | 5.0 mg |
| hydroxypropylmethylcellulose | 5.0 mg |
| NaOH 1N q.s. to pH = 7.4 | |
| distilled water q.s. to | 1.0 ml |

The solution ingredients are mixed together according to the procedures conventionally employed for the preparation of ophthalmic solutions.

EXAMPLE 6

Ophthalmic solution:

| | |
|---|---|
| Compound S | 1.0 mg |
| betamethasone sodium phosphate | 1.0 mg |
| NaH$_2$PO$_4$ | 10.4 mg |
| Na$_2$HPO$_4$ | 2.4 mg |
| chlorobutanol | 5.0 mg |
| hydroxypropylmethylcellulose | 5.0 mg |
| NaOH 1N q.s. to pH = 7.4 | |
| distilled water q.s. to | 1.0 ml |

The solution ingredients are mixed together according to the procedures conventionally employed for the preparation of ophthalmic solutions.

EXAMPLE 7

Pharmacological evaluation The pharmacological activity of the compounds of formula (I) according to the present invention, on intraocular pressure (IOP), has been evaluated in rabbits, using the experimental glaucoma model developed by L. Bonomi (1976). In this model a rapid increase in IOP is elicited in rabbits by fast i.v. injection of 15 mg/Kg of a 5 % glucose solution. The IOP reaches its maximum (29±1.6 mmHg) in 5 minutes, then it gradually returns to its almost normal value (22±1.6 mmHg) in 40 minutes. Females, Fauve de Bourgogne, pigmented rabbits (3±4 Kg) with a normal basal IOP at both eyes (19±0.6 mmHg) are employed in this test. They were instilled a single dose of 50 µl of an eye solution (either containing one of the products to be tested in physiological solution or the vehicle alone) in one eye, in blind [the other eye remained untreated and served as control). Ten minutes after this instillation, a second IOP measurement was done, and immediately after this measurement 15 mg/Kg of a 5% glucose solution was rapidly injected in the ear marginal vein. IOP measurements were then done 5, 10, 20, 30, and 40 minutes after the injection. IOPs were taken with a pneumotonometer. While instillation of the vehicle did not give raise to any significative difference in the IOP elevation curve, with respect to that of the untreated eyes, the results obtained with some representative compounds of the present invention show that the compounds of formula (I) are active on this model of acute glaucoma. As an example, by the instillation of Compound G (as the hydrochloride) the basal IOP value is not lowered within 10 minutes, while the maximum IOP value reached within 5 minutes is kept lower than 21±2.3 mmHg and IOP normal values are rapidly restored.

I claim:

1. A method for the prophylaxis and/or treatment of ocular hypertension and glaucoma in mammals which comprises administering to a mammal in need thereof a prophylactically or therapeutically effective amount of a phenylethanolamine derivative of formula (I)

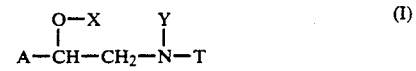

wherein
- A represents a phenyl group which is unsubstituted or substituted with one or two halogen atoms or with a lower alkyl or trifluoromethyl group;
- X represents hydrogen, lower alkyl or lower alkanoyl;
- Y represents hydrogen or a group A'-(CH(OH)-CH$_2$-, A' being identical to A; or
- X and Y, taken together, form a methylene bridge optionally substituted with a carbo(lower alkoxy) group an ethylene bridge optionally oxo-substituted; or a 1,3-propylene bride; and
- T represents a group of formula (II)

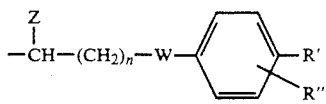

wherein

N is 1, 2, or 3;
Z is hydrogen or a lower alkyl group
W represents a direct bond or an oxygen atom;
R' represents
- hydrogen
- lower alkyl
- a functional group selected from the group consisting of: hydroxy; lower alkoxy; lower alkenyloxy; lower alkynyloxy; cycloalkyloxy; cycloalkyl-(lower alkoxy); benzyloxy; phenoxy; mercapto; (lower alkyl)thio; (lower alkenyl)thio; (lower alkynyl)thio; cycloalkylthio; cycloalkyl-(lower alkyl)thio; benzylthio; phenylthio; (lower alkyl)-sulfinyl (lower alkenyl)sulfinyl; (lower alkynyl)-sulfinyl; cycloalkylsulfinyl; cycloalkyl-(lower alkyl)sulfinyl; benzylsulfinyl phenylsulfinyl; (lower alkyl)sulfonyl; (lower alkenyl)sulfonyl; (lower alkynyl)sulfonyl; cycloalkylsulfonyl; cycloalkyl-(lower alkyl)sulfonyl; benzylsulfonyl; phenylsulfonyl; cyano; nitro; amino either unsubstituted or substituted with one or two radicals which are independently selected from the group consisting of lower alkyl, lower alkenyl, lower alkynyl, cycloalkyl, cycloalkyl-(lower alkyl), benzyl, and phenyl; carboxy; (lower alkoxy)carbonyl; (lower alkenyloxy)carbonyl; (lower alkynyloxy)carbonyl; cycloalkyloxycarbonyl; cycloalkyl-(lower alkoxy)carbonyl; benzyloxycarbonyl; phenoxycarbonyl; and carbamoyl either unsubstituted or substituted on the amino group with one or two radicals independently selected from the group consisting of lower alkyl, lower alkenyl, lower alkynyl, cycloalkyl, cycloalkyl(lower alkyl), benzyl, and phenyl;
- a radical -R selected from the group consisting of lower alkyl substituted with a functional group; lower alkenyl substituted with a functional group; lower alkynyl substituted with a functional group; phenyl-(lower alkyl) substituted on the phenyl ring with a lower alkyl or a functional group; phenyl-(lower alkenyl) substituted on the phenyl ring with a lower alkyl or a functional group; phenyl-(lower alkynyl) substituted on the phenyl ring with a lower alkyl or a functional group; benzyl substituted on the phenyl ring with a lower alkyl or a functional group; and phenyl either unsubstituted or substituted with a lower alkyl or a functional group and functional group being as defined above;
- a group -OR, -SO-R, or -SO₂R wherein R is as defined above;
- a group -NRR°, wherein R is as defined above and R° represents hydrogen or is as defined above for R;
- a —COOR or —COSR group, wherein R is as defined above;
- a group —CONRR°, wherein R is as defined above and R° represents hydrogen or is as defined above for R];
- a group —SO₂NRR°, wherein R is as defined above and R° represents hydrogen or is as defined above for R; and R" represents
- hydrogen;
- a hydrogen atom;
- a lower alkyl group;
- a functional group as defined above;
- a group-OR, wherein R is as defined above;
- a group -COOR, wherein R is as defined above;
- a group -CONRR°, wherein R is as defined above and R° represents hydrogen or is as defined above for R;

or
when X and Y are hydrogen atoms, T may also represent a group of formula (III)

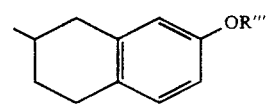

wherein
R''' represents hydrogen; methyl, or methyl substituted with carboxy or carbo(lower alkoxy);
or of one of its pharmaceutically acceptable salts.

2. The method of claim 1 wherein the phenylethanolamine derivative has formula (I) wherein
X and Y are hydrogen; and
T represents a group of formula (III) wherein R''' is as defined above.

3. The method of claim 2 wherein the phenylethanolamine derivative has formula (I) wherein
A is a 3-chlorophenyl group
X and Y are hydrogen; and
T represents a group of formula (III) wherein
R''' is hydrogen; carbomethoxymethyl; or carbethoxymethyl.

4. The method of claim 3 wherein the phenylethanolamine derivative is selected from the group consisting of
N-(7-hydroxy-1,2,3,4-tetrahydronaphth-2-yl)-2-(3chlorophenyl)-2-hydroxyethanamine and its pharmaceutically acceptable salts;
N--(2R)-2-(3-chlorophenyl)-2-hydroxyethanamine and its pharmaceutically acceptable salts;
N--(2R)-2-(3-chlorophenyl)-2-hydroxyethanamine and its pharmaceutically acceptable salts;
N---(2S)-2-(3-chlorophenyl)-2-hydroxyethanamine and its pharmaceutically acceptable salts;
N-(2S)-2-(3-chlorophenyl)-2-hydroxyethanamine and its pharmaceutically acceptable salts;
N--(2R)-2-(3-chlorophenyl)-2-hydroxyethaneamine and its pharmaceutically acceptable salts;
N--(2R)-2-(3-chlorophenyl)-2-hydroxyethaneamine and its pharmaceutically acceptable salts;
N--(2S)-2-(3-chlorophenyl)-2-hydroxyethanamine and its pharmaceutically acceptable salts; and
N--(2R)-2-(3-chlorophenyl)-2-hydroxyethanamine and its pharmaceutically acceptable salts.

5. The method of claim 1 wherein the phenylethanolamine derivative has formula (I) wherein
A is phenyl, 2-fluorophenyl, 3-chlorophenyl, or 3-trifluoromethylphenyl;
X is hydrogen;
Y is hydrogen or a group A'—CH(OH)—CH₂— wherein A' is the same as A and is phenyl, 2- fluorophenyl, 3-chlorophenyl, or 3trifluoromethyl-phenyl;
T is a group of formula (II) wherein
n is 1 or 2;
R, is
   a functional group selected from hydroxy; carboxy; carbo(lower alkoxy); and carbamoyl; or
   a group -OR wherein R is a lower alkyl or lower alkenyl group substituted with a functional group selected from carboxy and carbo(lower alkoxy);
R" is hydrogen;
W is a direct bond; and
Z is a lower alkyl group.

6. The method of claim 5 wherein the phenylethanolamine derivative has formula (I) wherein
A is phenyl, 3-chlorophenyl, or 3-trifluoromethyl-phenyl;
X is hydrogen;
Y is hydrogen or a group A'—CH(OH)—CH$_2$— wherein A' is the same as A and is phenyl;
T is a group of formula (II) wherein
n is 1 or 2;
R' is selected from the group consisting of hydroxy, carboxy, carbomethoxy, carbethoxy, carbamoyl, carboxymethoxy, carbomethoxymethoxy and carbethoxymethoxy;
R" is hydrogen;
W is a direct bond; and
Z is methyl.

7. The method of claim 6 wherein the phenylethanolamine derivative is selected from the group consisting of
N--2-hydroxy-2-phenylethylamine and its pharmaceutically acceptable salts;
N--2-h-ydroxy-2-phenylethylamine and its pharmaceutically acceptable salts;
(R,S)-N-(2-phenyl-2-hydroxyethyl)-1-methyl-3-(4-hydroxyphenyl)propylamine and its pharmaceutically acceptable salts;
(R,S)-N-(2-phenyl-2-hydroxyethyl)-1-methyl-3-(4-aminocarbonylphenyl)propylamine and its p-harmaceutically acceptable salts;
p-benzamide and its pharmaceutically acceptable salts;
(RR,SS)-N---2-hydroxy-2-(3-trifluoromethylphenyl)ethanamine and its pharmaceutically acceptable salts;
(RR,SS)-N---2-hydroxy-2-(3-trifluoromethylphenyl)ethanamine and its pharmaceutically acceptable salts; and
N--2-hydroxy-2-(3-chlorophenyl)ethanamine and its pharmaceutically acceptable salts; and
p--benzamide, and its pharmaceutically acceptable salts;
N--2-hydroxy -2 -(3 chlorophenyl)ethanamine, and its pharmaceutically acceptable salts.

8. The method of claim 7 wherein the phenylethanolamine derivative is the lower melting diastereoisomer mixture of N--2-hydroxy-2-phenylethylamine neutral fumarate.

9. The method of claim 7 wherein the phenylethanolamine derivative is (RR,SS)-N---2-hydroxy-2-[3-chlorophenyl)ethan -amine or its hydrobromide.

10. The method of claim 1 wherein the phenylethanolamine derivative is administered topically in the eye.

11. The method of claim 10 wherein the phenylethanolamine derivative is administered in an amount comprised between 10 ng and 1 mg per day.

12. The method of claim 11 wherein the phenylethanolamine derivative is administered in an amount comprised between 100 ng and 0.2 mg per day.

* * * * *